(12) United States Patent
Teague et al.

(10) Patent No.: US 8,556,948 B2
(45) Date of Patent: Oct. 15, 2013

(54) STERNAL CLAMP WITH RIB EXTENSION

(75) Inventors: Mike Teague, Ponte Vedra Beach, FL (US); Charles Anderson, Gig harbor, WA (US); Shawn Burke, Atlantic Beach, FL (US); Axel Walzenegger, Muhlheim, DE (US)

(73) Assignee: KLS-Martin, L.P., Jacksonville, FL (US)

( * ) Notice: Subject to any disclaimer, the term of this patent is extended or adjusted under 35 U.S.C. 154(b) by 0 days.

(21) Appl. No.: 13/490,181

(22) Filed: Jun. 6, 2012

(65) Prior Publication Data

US 2012/0245644 A1 Sep. 27, 2012

Related U.S. Application Data

(62) Division of application No. 12/383,103, filed on Mar. 19, 2009, now abandoned.

(60) Provisional application No. 61/069,982, filed on Mar. 19, 2008.

(51) Int. Cl.
*A61B 17/04* (2006.01)
*A61B 17/84* (2006.01)
*A61F 2/08* (2006.01)

(52) U.S. Cl.
USPC ............ 606/324; 606/326; 606/328; 606/330

(58) Field of Classification Search
USPC ........................................................ 606/324
See application file for complete search history.

(56) References Cited

U.S. PATENT DOCUMENTS

| 4,085,744 | A | 4/1978 | Lewis et al. |
| 7,033,377 | B2 | 4/2006 | Miller, III |
| 2007/0043371 | A1 | 2/2007 | Teague et al. |
| 2009/0204149 | A1 | 8/2009 | Malek |

*Primary Examiner* — Nicholas Woodall
*Assistant Examiner* — Christine Nelson
(74) *Attorney, Agent, or Firm* — Thomas C. Saitta

(57) ABSTRACT

A sternal closure clamp device for securing and retaining longitudinally divided halves of a sternum, and its method of use, the device having a pair of body members each having engagement members adapted to abut the sides of the sternal halves, and at least one rib extension member having rib retaining members and attached to at least one of said body members, such that the rib extension member can be secured to a rib to reduce the force being applied directly to the sternal halves.

8 Claims, 2 Drawing Sheets

STERNAL CLAMP WITH RIB EXTENSION

This application is a divisional application of U.S. patent application Ser. No. 12/383,103, filed Mar. 19, 2009, claiming the benefit of U.S. Provisional Patent Application Ser. No. 61/069,982, filed Mar. 19, 2008.

BACKGROUND OF THE INVENTION

This invention generally relates to devices used to rejoin a human sternum that has been severed longitudinally, and more particularly relates to such devices that function in a clamping manner to retain the severed sternum portions in a closed and abutting relationship post-operatively.

It is often necessary in surgical operations to longitudinally sever the patient's sternum so that the ribs may be spread to provide access to internal organs such as the heart. It is then necessary to secure the sternum halves together for post-operative recovery. Various closure techniques are used to accomplish this task. For example, holes may be drilled into the sternum halves and suture material passed through and tightened to cinch the sternum halves together. Apertured plates may be added to further rigidify the sternum post-operatively, with the suture material being passed through the apertures in the plate and the sternum. Encircling members may be wrapped around the sternum and tightened. Toothed bridging members extending across the cut line may be pressed into the sternum surfaces and/or secured with threaded rods extending between the sternal halves.

Another sternal closure technique involves the use of clamps having hook-like projections or engagement members on both ends, the clamp being positioned laterally relative to the sternal incision with the projections being disposed between adjoining rib pairs on opposite sides of the sternum. The clamp is then linearly contracted or compressed to shorten the device and force the sternal halves together, the clamp typically comprising two members joined in a linearly telescoping manner. Locking or securing means, either permanent or releasable, maintain the clamp in the contracted configuration so that the sternum can heal.

Examples of such techniques and devices are described in U.S. Pat. No. 3,473,528 to Mishkin et al., U.S. Pat. No. 4,201,215 to Crossett et al., U.S. Pat. No. 4,279,248 to Gabbay, U.S. Pat. No. 4,583,541 to Barry, U.S. Pat. No. 5,139,498 to Astudillo Ley, U.S. Pat. No. 6,051,007 to Hogendijk et al., U.S. Pat. No. 6,217,580 to Levin, U.S. Pat. No. 6,302,899 to Johnson et al., U.S. Pat. No. 6,540,769 to Miller, III, and U.S. Pat. No. 6,712,821 to Gabbay the disclosures of which are herein incorporated by reference.

In certain circumstances, the strength and rigidity of the sternum may be insufficient to withstand the compressive forces of the sternal clamp, such that the sternum may be damaged upon compression of the sternal clamp or such that overtime the weakness of the sternum results in damage from the clamp. It is an object of this invention to provide a sternal closure clamp device having at least one rib extension member such that the clamp may be secured directly to the rib a distance away from the sternum, such that the compressive forces of the sternal clamp are dispersed between the sternum and the rib.

SUMMARY OF THE INVENTION

The invention is in general a sternal closure clamp device for closing, securing and supporting a patient's sternum that has been longitudinally severed into two sternal halves, and its method of use. The sternal clamp generally comprises two body members each preferably having a pair of spaced, sternum-engaging engagement members extending rearward from the body member.

The engagement members are means to engage, secure or otherwise retain the sternal halves in an abutting relationship, with the engagement members comprising hooks, projections, fingers or the like extending in the posterior direction, whereby the engagement members can be disposed against the outer edges of the sternal halves and between adjoining ribs, preferably with the two engagement members located on a given side being positioned in the inter-rib spaces to either side of a single rib.

Extending from at least one of the two body members is a rib extension member, the rib extension member preferably being attached to the body member in a pivoting manner such that the angle of the rib extension relative to the body member can be adjusted. Rib securing or clamping members are provided on the free end of the rib extension arm member such that the device can be securely affixed to the rib.

DETAILED DESCRIPTION OF THE INVENTION

With reference to the drawings, the invention will now be described in detail with regard for the best mode and the preferred embodiment. The invention is a sternal closure methodology and clamp device used to close, secure and support a sternum, the sternum having been severed longitudinally into left and right lateral sternal halves to provide access to the interior of the chest, wherein the sternal clamp comprises two opposing body members and a rib extension member mounted to at least one of said body members.

The sternal clamp 10 generally comprises two opposing body members 11 and 12 each at least one and preferably a pair of spaced, sternum-engaging engagement members 13 extending posteriorly from the body members 11 and 12. The body members 11 and 12 are slidingly or telescopically interconnected such that the overall length of the sternal clamp 10 can be adjusted. The engagement members 13 are means to engage, secure or otherwise retain the sternal halves in an abutting relationship, with the engagement members 13 comprising hooks, projections, fingers or the like extending in the posterior direction from the main bodies 11 and 12, whereby the engagement members 13 are able to be disposed against the outer edges of the sternal halves and between adjoining ribs, preferably with the two engagement members 13 located on a given side being positioned in the inter-rib spaces to either side of a single rib. In use, the clamp 10 is positioned on the sternal halves across the longitudinal sternal incision with the engagement members 13 located in the inter-rib spaces, such that at least one rib is between the two engagement members 13 on a given side of the clamp 10. The sternal halves and opposing body members 11 and 12 are forced or drawn together to close the longitudinal incision, such that the sternal halves are retained in an abutted relation by the engagement members 13 and precluded from separating, the clamp 10 comprising means (not shown) to retain or lock the clamp 10 in the compressed or contracted position, such as a mechanical fastener, ratchet mechanisms, springs or the like. Such sternal clamps are well known in the art.

Figure 1:
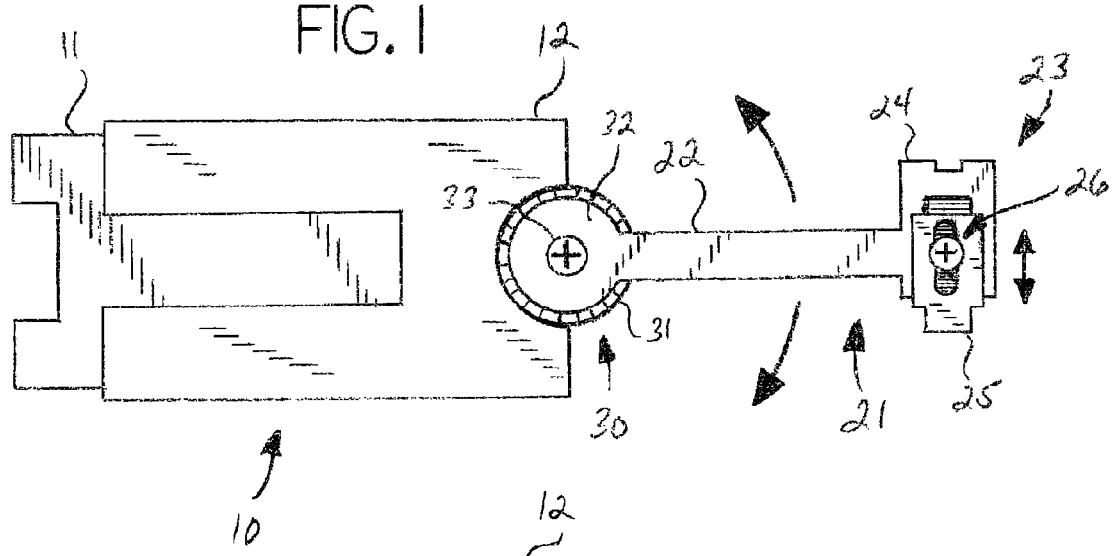
FIG. 1 is a front view of an embodiment of the invention.
Figure 2:
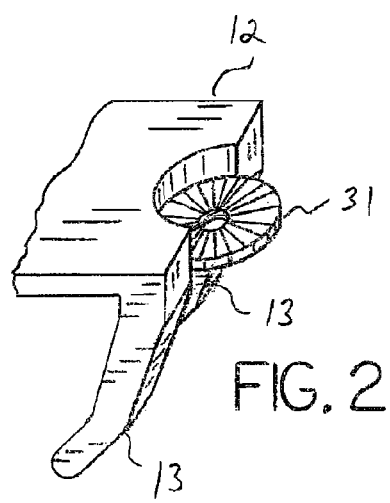
FIG. 2 is a front perspective view of a portion of the embodiment of FIG. 1, showing the mounting platform for the rib extension member.
Figure 3:
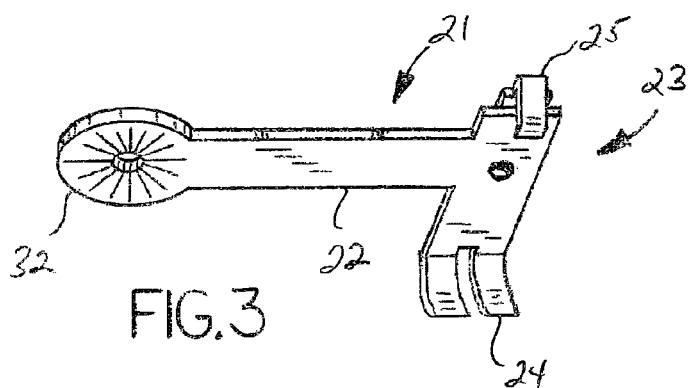
FIG. 3 is a rear perspective view of the rib extension member of the embodiment of FIG. 1.
Figure 4:
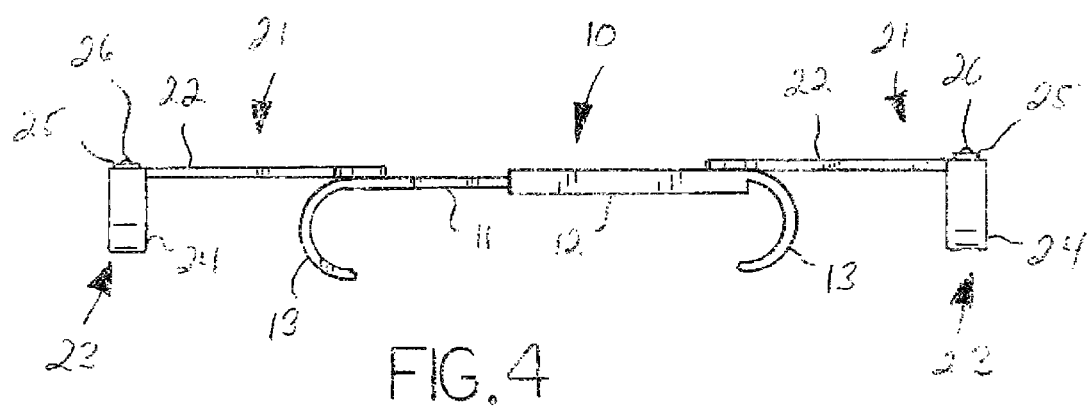
FIG. 4 is a side view of an embodiment of the invention having two rib extension members.

To address the circumstances where the sternum bone material is not strong enough to withstand the compressive force of the sternal clamp 10, due to age, injury, disease or the like, the sternal clamp 10 comprises a rib extension member 21 attached to at least one body member, herein shown in FIGS. 1 and 2 as attached to body member 12. A second rib extension member 21 could also be attached to body member 11, as shown in FIG. 4, or alternatively plural rib extension members 21 could be mounted on one side. The rib extension member 21 may be rigidly affixed to the body member 12, but preferably is mounted onto body member 12 by means 30 for pivoting the rib extension member 21 such that the relative angle between the rib extension member 21 and body member 12 can be altered. As a representative non-limiting example, in the drawings the pivot means 30 is shown to comprise an apertured base plate member 31 positioned on the body member 12, an apertured arm plate member 32 positioned on the end of arm member 22, and fastener means 33, such as a screw, designed to secure the arm plate member 32 to the base plate member 31.

The rib extension member 21 further comprises rib securing members 23 positioned on the free end of arm member 22, the rib securing members 23 being adapted to secure the rib extension member 21 directly onto a rib at a point distanced from the sternum and body member 12. Rib securing members 23 may comprise any suitable clamping or fastening structure, and a non-limiting representative example is shown in the drawings to comprise at least one fixed projection or leg member 24, an adjustable projection or leg member 25 and securing means 26, such as a screw, that allows the legs 24 and 25 to be clamped tightly onto the rib by spreading apart or extending the leg members 25 and 26, forcing them together to securely abut the rib, and locking them in place about the rib.

To utilize the device, after the sternum has been longitudinally severed to produce two sternal halves, the clamp 10 is extended and placed about the sternal halves such that the projection members 13 abut the outer sides of the sternal halves. Arm member 22 may be bent, angled or curved toward the front or rear to conform to the position of the rib to which it will be attached. The rib extension member 21 is pivoted to properly align it with the rib and the rib securing members 23 are secured to the rib. The sternal halves are then drawn together and the clamp 10 is locked so that it cannot be extended. In this manner, the compressive force of the sternal clamp 10 is divided between the sternum and the rib (or ribs) when the clamp 10 is positioned about the sternal halves and contracted, as opposed to being completely concentrated against the sternal bone.

It is understood that equivalents and substitutions to elements set forth above may be obvious to one of ordinary skill in the art, and therefore the true scope and definition of the invention is to be as set forth in the following claims.

We claim:

1. A method of securing the longitudinally severed halves of a sternum in abutting relation comprising the steps of:
   providing a sternal clamp comprising a first body member and a second body member, said first body member and said second body member slidingly interconnected to each other whereby the overall length of said clamp is adjustable, a pair of sternal engagement members connected to each of said first body member and said second body member, said sternal engagement members extending to the rear of each of said body members, and a first rib extension member connected to said first body member between said pair of sternal engagement members, said first rib extension member extending beyond said first body member and comprising rib securing members adapted to secure said first rib extension member directly onto a rib; whereby each of said pairs of sternal engagement members is configured to abut the outer side of a longitudinally severed halve of a sternum and to receive a rib therebetween, and whereby said first rib extension member is securable directly onto one said rib;
   positioning said clamp across said longitudinally severed halves of said sternum such that said pairs of sternal engagement members abut the outer sides of said longitudinally severed halves of said sternum and such that each said pair of sternal engagement members receives a rib therebetween;
   securing said first rib extension member to one of said ribs;
   contracting said clamp to draw said longitudinally severed halves of said sternum into abutting relation; and
   locking said clamp to secure said longitudinally severed halves of said sternum in abutting relation.

2. The method of claim 1, wherein said first rib extension member is angularly adjustable relative to said first body member; and further comprising the step of:
   angularly adjusting said first rib extension member prior to said step of securing said first rib extension member to one of said ribs.

3. The method of claim 1, said clamp further comprising a second rib extension member connected to said second body member between said pair of sternal engagement members of said second body member, said second rib extension member extending beyond said second body member and comprising rib securing members adapted to secure said second rib extension member directly onto one of said ribs; and further comprising the step of:
   securing said second rib extension member to one of said ribs prior to said step of contracting said clamp.

4. The method of claim 2, said clamp further comprising a second rib extension member connected to said second body member between said pair of sternal engagement members of said second body member, said second rib extension member extending beyond said second body member and comprising rib securing members adapted to secure said second rib extension member directly onto one of said ribs; and further comprising the steps of:
   angularly adjusting said second rib extension member prior to said step of securing said second rib extension member to one of said ribs;
   securing said second rib extension member to one of said ribs prior to said step of contracting said clamp.

5. A method of surgery comprising the steps of:
   longitudinally severing a sternum into two sternal halves, each said sternal half having ribs connected thereto;
   providing a sternal clamp comprising a first body member and a second body member, said first body member and said second body member slidingly interconnected to each other whereby the overall length of said clamp is adjustable, a pair of sternal engagement members connected to each of said first body member and said second body member, said sternal engagement members extending to the rear of each of said body members, and a first rib extension member connected to said first body member between said pair of sternal engagement members, said first rib extension member extending beyond said first body member and comprising rib securing members adapted to secure said first rib extension member directly onto one of said ribs; whereby each of said pairs of sternal engagement members is configured to abut the outer side of one said sternal halve and to receive one of said ribs therebetween, and whereby said first rib extension member is securable directly onto one of said ribs;

positioning said clamp across said sternal halves such that said pairs of sternal engagement members abut the outer sides of said sternal halves and such that each said pair of sternal engagement members receives one of said ribs therebetween;

securing said first rib extension member to one of said ribs;

contracting said clamp to draw said sternal halves into abutting relation; and locking said clamp to secure said sternal halves of said sternum in abutting relation.

6. The method of claim 5, wherein said first rib extension member is angularly adjustable relative to said first body member; and further comprising the step of:

angularly adjusting said first rib extension member prior to said step of securing said first rib extension member to one of said ribs.

7. The method of claim 5, said clamp further comprising a second rib extension member connected to said second body member between said pair of sternal engagement members of said second body member, said second rib extension member extending beyond said second body member and comprising rib securing members adapted to secure said second rib extension member directly onto one of said ribs; and further comprising the step of:

securing said second rib extension member to one of said ribs prior to said step of contracting said clamp.

8. The method of claim 6, said clamp further comprising a second rib extension member connected to said second body member between said pair of sternal engagement members of said second body member, said second rib extension member extending beyond said second body member and comprising rib securing members adapted to secure said second rib extension member directly onto one of said ribs; and further comprising the steps of:

angularly adjusting said second rib extension member prior to said step of securing said second rib extension member to one of said ribs;

securing said second rib extension member to one of said ribs prior to said step of contracting said clamp.

\* \* \* \* \*